United States Patent [19]

Black

[11] Patent Number: 5,434,137

[45] Date of Patent: Jul. 18, 1995

[54] METHOD FOR SELECTIVE OPENING OF ABNORMAL BRAIN TISSUE CAPILLARIES

[76] Inventor: Keith L. Black, 1233 Roberto La., Los Angeles, Calif. 90077

[21] Appl. No.: 59,623

[22] Filed: May 10, 1993

[51] Int. Cl.$^6$ .................. G01N 1/00; A61K 38/00
[52] U.S. Cl. .................................. 514/15; 514/17
[58] Field of Search .................... 514/15, 17

[56] References Cited

U.S. PATENT DOCUMENTS 5,112,596  5/1992  Malfroy-Camine ............ 514/17 X
5,268,164  12/1993  Kozarich et al. .................. 424/9

OTHER PUBLICATIONS

Wahl, et al. (1987) "Effects of Bradykinin on Cerebral Haemodynamics and Blood-Brain Barrier Function", In *Peptidergic Mechanisms in the Cerebral Circulation* (Edvinsson, L. and McCulloch, J., Eds.) Chichester, Horwood, pp. 166–190.
Wahl, et al. (1988) "Mediators of Blood-Brain Barrier Dysfunction and Formation of Basogenic Brain Edema", *J. Cerebral Blood Flow and Metabolism*, 8:621–634.
Raymond, et al. (1986) "Pharmacological Modification of Bradykinin Induced Breakdown of the Blood-Brain Barrier", *Can. J. Neur. Sci.*, 13:214–220.
Wahl, et al. (1986) "Cerebrovascular Effects of Bradykinin," in *Neural Regulation of Brain Circulation* (Owman, C. and Hardebo, J. E. Eds), Elsevier Science Publishers B.V., pp. 419–430.
Unterberg, et al. (1984) "Effects of Bradykinin on Permeability and Diameter of Pial Vessels in Vivo," *J. Cerebral Blood Flow and Metabolism*, 4:574–585.
Black, et al. (1992) "Increased Opening of Blood-Tumor Barrier by Leukotriene $C_4$ is Dependent on Size of Molecules," *Neurological Research*, 14: 402–404.
Black, et al. (1990) "Selective Opening of the Blood-Tumor Barrier by Intracarotid Infusion of Leukotriene $C_4$," *J. Neurosurg.*, 72:912–916.
Baba, T., et al. (1991) "Intracarotid Infusion of Leukotriene $C_4$ Selectively Increases Blood-Brain Barrier Permeability After Focal Ischemica in Rats," *Journal of Cerebral Blood Flow and Metabolism*, 11:638–643.
Chio, et al. (1992) "Selective Blood-Tumor Barrier Disruption by Leukotrienes," *J. Neurosurg.*, 77:407–410.

*Primary Examiner*—Howard E. Schain
*Assistant Examiner*—P. Lynn Touzeau
*Attorney, Agent, or Firm*—Poms, Smith, Lande & Rose

[57] ABSTRACT

A method for selectively opening abnormal brain tissue capillaries of a mammal in order to allow selective passage of both low and high molecular weight neuropharmaceutical agents into abnormal brain tissue. The method utilizes direct infusion of bradykinin into the carotid artery. The dose of bradykinin is maintained at levels which provide opening of abnormal brain tissue capillaries without opening normal brain capillaries. The method is useful for introducing a wide variety of neuropharmaceutical agents selectively to brain tumors and other abnormal brain tissue.

6 Claims, 3 Drawing Sheets

METHOD FOR SELECTIVE OPENING OF ABNORMAL BRAIN TISSUE CAPILLARIES

BACKGROUND OF THE INVENTION

1. Field of the Invention

The present invention relates generally to methods for increasing the permeability of the blood brain barrier in order to introduce neuropharmaceutical agents into the brain. More particularly, the present invention is directed to a method which selectively increases permeability of the blood brain barrier in abnormal brain tissue.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Capillaries within the brain include a barrier which prevents the delivery of many pharmaceutical agents to the brain. This blood-brain barrier (BBB) is present in both normal and abnormal brain tissue. The treatment of brain tissue abnormalities, such as tumors, require that the neuropharmaceutical agent be preferentially directed to the abnormal tissue. Accordingly, there has been a great deal of interest in developing techniques which are capable of opening the blood-brain barrier to allow transport of neuropharmaceutical agents to the brain (1, 2, 3, 4 and 5). None of these methods, however, are capable of selectively opening the blood-brain barrier only in the abnormal brain while leaving the blood-brain barrier in the normal brain intact.

In previous studies, it was demonstrated that intracarotid infusion of leukotriene $C_4$ ($LTC_4$) selectively increases the permeability in brain tumor capillaries without affecting the permeability in normal brain capillaries (6–9). The effect of $LTC_4$ on brain tumor capillaries is, however, limited to small molecules and it can only slightly increase the permeability of those small molecules in abnormal brain tissue. Accordingly, $LTC_4$ does not significantly increase the delivery of some water soluble drugs to brain tumors (10–13).

Bradykinin is a naturally occurring peptide formed from a plasma protein, high molecular weight kininogen by the action of kallikarein. Bradykinin is a very powerful vasodilator that increases capillary permeability. In addition, bradykinin constricts smooth muscle and stimulates pain receptors. Bradykinin may reduce cerebral blood flow (14, 15) and, in high doses will induce breakdown of the normal blood brain barrier (16). U.S. Pat. No. 5,112,596 discloses the intravenous administration of bradykinin to provide a general increase of blood-brain barrier permeability which is not selective with respect to tumors or other abnormal brain tissue.

In view of the above, there is a continuing need to develop methods for selectively opening abnormal brain tissue capillaries in order to allow selective passage of neuropharmaceutical agents into abnormal brain tissue without increasing the permeability of the normal blood-brain barrier.

SUMMARY OF THE INVENTION

In accordance with the present invention, it was discovered that intracarotid artery infusion of low doses of bradykinin selectively increases the permeability of abnormal brain tissue capillaries to both low and high molecular weight neuropharmaceutical agents. Infusion of bradykinin into the carotid artery has previously been thought to be a drastic measure which, like cortical superfusion, is not to be used with powerful drugs such as bradykinin except in extreme cases.

Contrary to prior thinking, the present invention involves a method wherein bradykinin, at low dosages, is infused directly into the carotid artery. It was discovered that such infusion of low levels of bradykinin selectively open abnormal brain tissue capillaries without opening normal brain capillaries. It was discovered that the abnormal brain capillaries are opened sufficiently by intracarotid infusion of bradykinin to allow the passage of a variety of molecular weight, (i.e. about 100 to about 70,000) neuropharmaceutical agents into the abnormal brain tissue.

As a feature of the present invention, neuropharmaceutical agents can be co-administered with the bradykinin to provide selective delivery of the neuropharmaceutical agent to abnormal brain tissues such as tumors and cerebral abscesses.

The above discussed and many other features and attendant advantages will become better understood by reference to the following detailed description when taken in conjunction with the accompanying drawings.

DETAILED DESCRIPTION OF THE PREFERRED EMBODIMENTS

Figure 1:
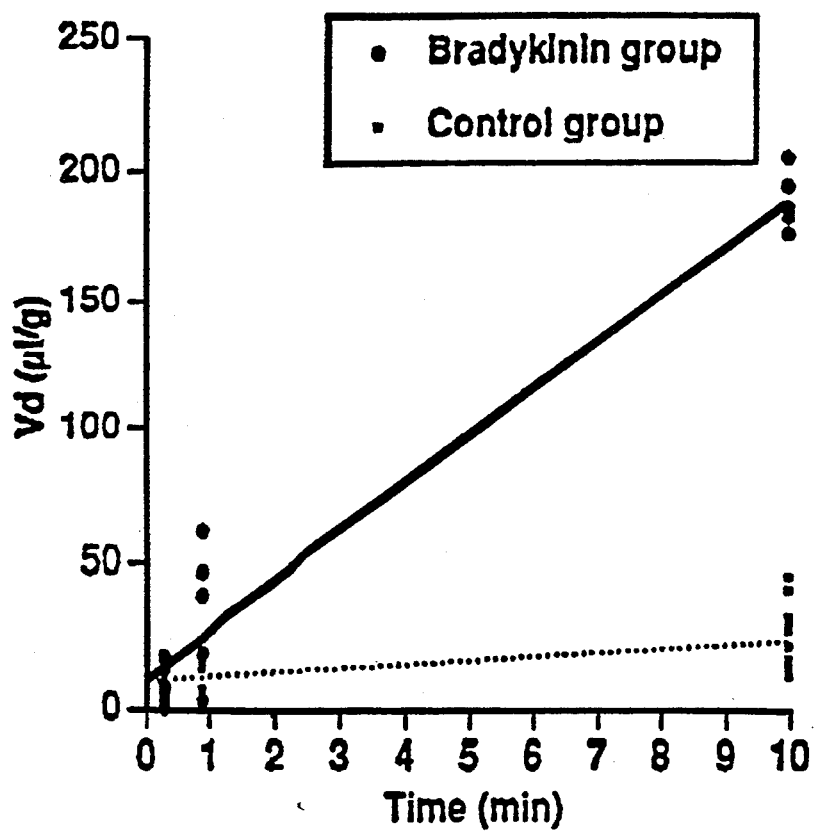
FIG. 1 is a graph showing that the selective increase in the volume of distribution in brain tumors is due to an increase in tumor permeability and not blood volume when treated with bradykinin in accordance with the present invention.

The present invention is a method for selectively opening abnormal brain tissue capillaries of a mammal in order to allow selective passage of both low and high molecular neuropharmaceutical agents into the abnormal brain tissues. The present invention is applicable to treating brain tumors, abnormal tissues resulting from multiple sclerosis, ischemia and cerebral abscess. The invention is also applicable to brain tissue which is inflamed, infected or degenerated due to any number of different diseases.

The method involves opening the abnormal brain tissue capillaries by infusing bradykinin or a bradykinin analog into the carotid artery of the mammal. The bradykinin or bradykinin analog is infused in an amount which is sufficient to selectively open the abnormal brain tissue capillaries to allow passage of neuropharmaceutical agents, including high molecular weight agents, into the abnormal brain tissue without opening the normal brain capillaries to passage of the neuropharmaceutical agent.

Bradykinin is a naturally occurring peptide comprised of nine amino acids. The structure of bradykinin and methods for isolating and purifying bradykinin are known. Analogs of bradykinin include related peptide structures which exhibit the same properties as bradykinin but have modified amino acids or peptide extensions on either terminal end of the peptide. Examples of bradykinin analogs include [phe$^8$ (CH$_2$—NH) Arg$^9$]—bradykinin, N-acetyl [phe$^8$ (CH$_2$—NH —Arg$^9$] bradykinin and desArg$^9$-bradykinin.

The amount of bradykinin which is infused into the carotid artery in order to selectively open the abnormal brain tissue capillaries to allow passage of neuropharmaceutical agents through the BBB may be varied depending upon the particular abnormal tissue being treated and the patient weight. The preferred dosage ranges from between 0.05 μg/kg body weight/minute to about 20 μg/kg body weight/minute. The total amount of bradykinin which is infused into the carotid artery during any single treatment is preferably kept below about 400 μg/kg body weight. For treating most abnormal tissues, the rate at which bradykinin is infused into the carotid artery will be on the order of about 10 μg/kg body weight/minute.

It is preferred that the bradykinin is infused into the carotid artery over a relatively short time period on the order of about 5 minutes to about 20 minutes. The selective opening of the abnormal brain tissue capillaries resulting from the infusion lasts for approximately 20 minutes after the bradykinin is administered. During this time period, a neuropharmaceutical agent may be introduced intravenously or also through the carotid artery. The selectively open abnormal brain tissue capillaries allow passage of the neuropharmaceutical agent into the abnormal brain tissue for treatment.

Any of the well known neuropharmaceutical agents may be administered in accordance with the present invention. Low molecular weight (100–20,000) as well as high molecular weight (about 20,000 to 70,000) neuropharmaceutical agents may be used. In addition to neuropharmaceutical agents, diagnostic agents may be used including imaging or contrast agents. Exemplary diagnostic agents include substances that are radioactively labelled such as 99-Tc glucoheptonate, gallium-EDTA, ferrous magnetic or iodinated contrast agents. Exemplary neuropharmaceutical agents include antibiotics, adrenergic agents, anticonvulsants, nucleotide analogs, chemotherapeutic agents, anti-trauma agents and other classes of agents used to treat or prevent neurological disorders. Specific neuropharmaceutical agents which can be administered into abnormal brain tissue in accordance with the present invention include cisplatin, carboplatin, methotrexate, 5-FU, amphotercin, immunotoxins, boron compounds, and monoclonal antibodies.

The bradykinin is administered into the carotid artery by any of the well known infusion techniques. For example, the bradykinin may be directly infused into the carotid artery by the following preferred procedure used for cerebral angiography where a catheter is inserted into the femoral artery and directed using fluoroscopic X-rays into the internal cartod artery or a more distal cerebral artery.

The bradykinin is preferably infused in the form of a pharmaceutical solution dissolved in 0.9% saline at a concentration of approximately 10–40 μg/ml. Any of the well known pharmaceutical carriers may be used as a diluent for the bradykinin to provide a solution which can be infused directly into the carotid artery.

Although the present invention is applicable to selectively treating a wide variety of abnormal brain tissues, the following examples will be limited to a demonstration of the invention with respect to brain tumors with it being understood by those skilled in the art that the invention is not so limited.

Examples of practice are as follows.

An experimental brain tumor model was made using female Wyster rats and RG-2 glioma cells. The RG-2 glioma cell line was maintained in a monolayer culture in F12 medium with 10% calf serum. Female Wyster rats, each weighing 150 to 250 gm were anesthetized with intra peritoneal pentobarbital (30 mg/kg). Glial tumors were implanted into the right hemisphere by intracerebral injections of $1 \times 10^5$ RG-2 glioma cells in five μl of 1.2% methyl cellulose (F12 medium). One week after tumor implantation, the rats were used for the brain tumor model.

The rats were divided into two groups: a bradykinin group treated with intracarotid infusion of 10 microliters/kg/min of bradykinin or the control group treated with intracarotid infusion of saline. The effect of intracarotid infusion of bradykinin was compared to saline infusions by statistical analysis of the Ki values using ANOVA and Students T-Tests.

It was determined that the 10 μl/kg/min dose of bradykinin dissolved in 0.9% saline did not alter systemic blood pressure. At infusion rates greater than 20 μg/kg/min the systemic blood pressure in the rats was reduced.

The blood volume for the quantitative examination of permeability was calculated with a graphic method using [$^{14}$X] dextran (MW 70,000). The blood volume in normal brain tissue and tumors were 4.5 and 9.15 μl/g, respectively (FIG. 1). The slopes were the unidirectional transfer constants, the Ki values (μl/g/min), in the two groups. The slope of the line of the rats treated with bradykinin indicated that the increased volume of distribution resulted from increased permeability and not from increased blood volume. The tumor blood volume was almost twice that of the normal brain tissue, but the brain and tumor blood volumes were not altered by intracarotid bradykinin infusion.

Figure 2A:
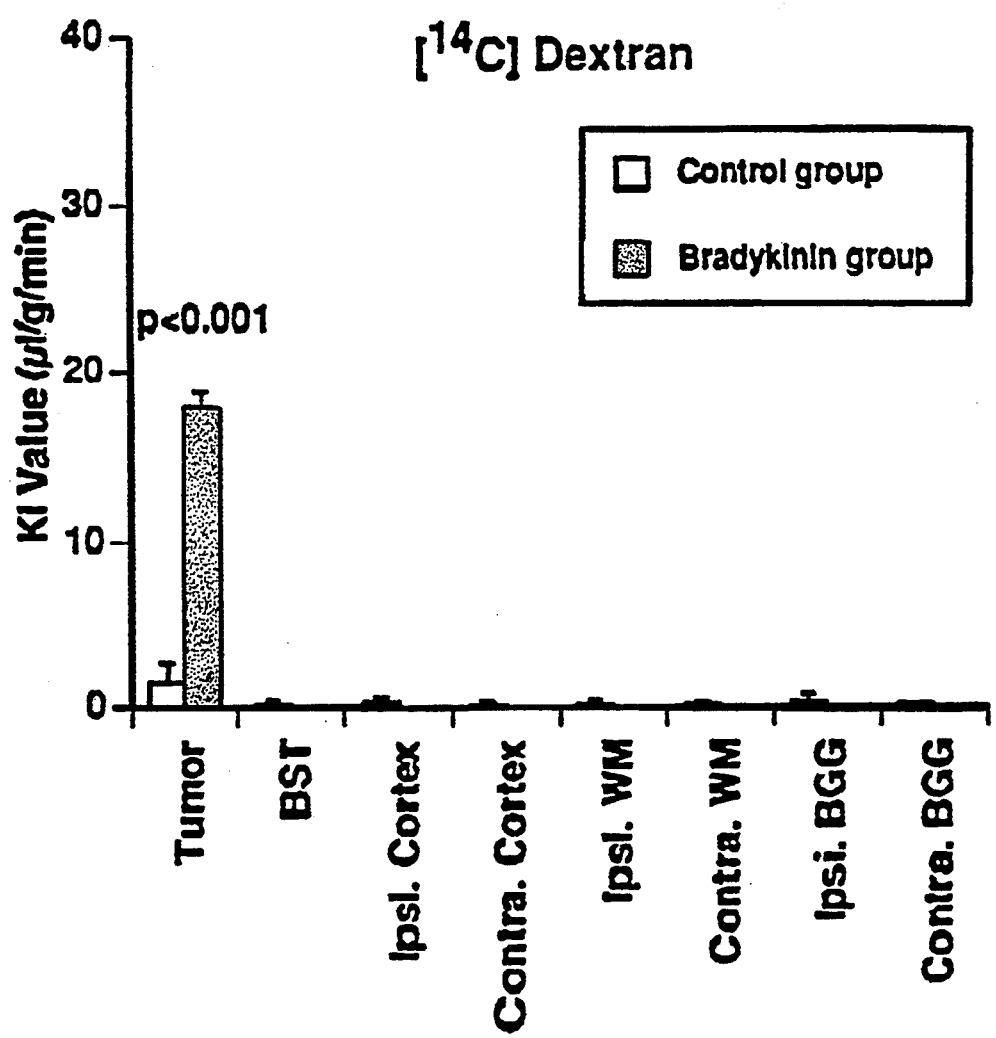
FIG. 2A is a graph which summarizes test results showing the selective uptake of dextran by brain tumor tissue in accordance with the method of the present invention. Bradykinin selectively increased permeability within the tumor 12-fold without increasing permeability in brain surrounding tumor (BST), ipsilateral normal cortex (ipsi cortex) contralateral normal cortex (contra cortex) ipsilateral white matter (ipsiwm) contralateral white matter (contra wm) or ipsilaterial or contralateral basal ganglia (BGG).

[$^{14}$C] AIB and [$^{14}$C] Dextran were used for quantitative autoradiographic examination of regional permeability. One week after tumor implantation, the rats were again anesthetized and a polyethylene (PE-10) catheter was inserted retrograde through the external carotid artery to the common carotid artery bifurcation ipsilateral to the tumor. The external carotid artery was then ligated. One femoral artery was cannulated to monitor systemic blood pressure and the other femoral artery was cannulated to withdraw arterial blood. Body temperature was maintained at 30° C. and arterial blood gas levels, blood pressure, hematocrit were monitored. Animals with abnormal physiological parameters were eliminated. After rat preparation, bradykinin (10μg/Kg/min in saline) or saline as control was infused into the right carotid artery at a rate of 53.3 μl/min for 15 minutes. Five minutes after the start of the intracarotid infusion, 100 μCi/Kg of the tracer was injected as an intravenous bolus. A peristaltic withdrawal pump was used to withdraw femoral arterial blood at a constant rate of 0.083 ml/min immediately after injection of tracer for determination of serum radioactivity. Fifteen minutes after the start of intracarotid infusions, the animals were killed by decapitation and the brains were rapidly removed and frozen. The regional permeability in the brains and tumor tissues were expressed by the unidirectional transfer constant, Ki value (μl/g/min). The Ki value of the tumors for [$^{14}$C] dextran (MW 70,000) in the bradykinin group was 12-fold higher than that for the control group (Mean±SD; 17.84±1.00 vs. 1.47±1.24; $p<0.001$) (FIG. 2A). This Ki value corresponded well with the Ki value derived from the slope in FIG. 1.

Figure 2B:
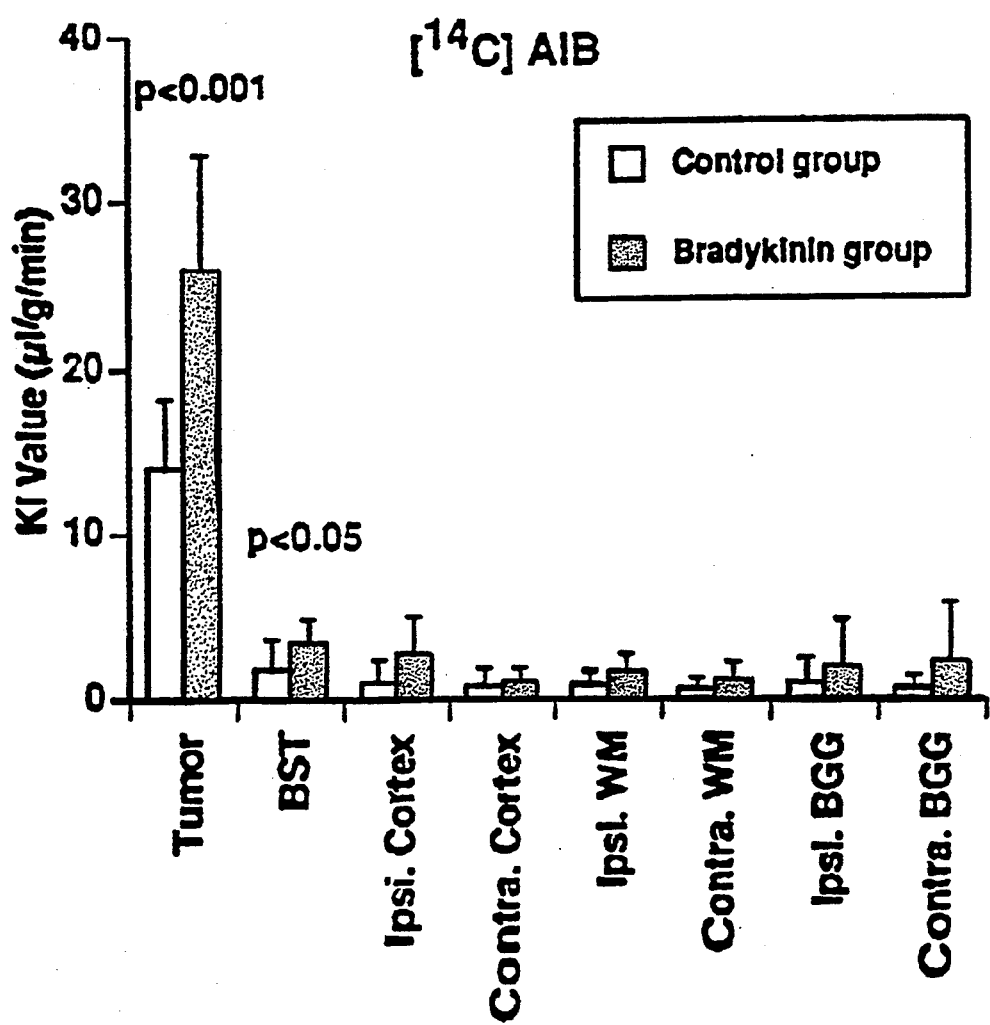
FIG. 2B depicts test results showing selective uptake of aminoisobuturic acid (AIB) by brain tumor tissue in accordance with the method of the present invention. In contrast to dextran, which has a molecular weight of 70,000, AIB has a molecular weight of 100.

The Ki values of brain regions without tumor in either bradykinin treated or control groups were very low and there was no significant difference between the two groups. The Ki value of the tumors for [$^{14}$C] AIB (MW 103) in the bradykinin group was 1.8-fold higher than that for the control group (25.91±6.78 vs. 13.95±4.29; $p<0.001$ (FIG. 2B). The Ki value of the brain surrounding tumor (BST; areas at 2 mm distance from the border of the tumor) for [$^{14}$C] AIB for the bradykinin group was also higher than that for the control group (3.50±1.29 vs. 1.83±1.78; $p<0.05$). This result shows that the effect of bradykinin on brain tumor capillaries is selective and the effect is more profound as the size of the tracer molecule increases.

Bradykinin has a short biological half-life because of its proteolytic inactivation (17). To determine the duration of the bradykinin effect on tumor capillary permeability, the Ki at three different time periods was measured. The rat preparation was the same as described above. The Ki value was measured in three different periods by changing the time of [$^{14}$C] dextran injection as also previously described. The three periods were as follows: 0 to 10 min during the intracarotid bradykinin infusion, 0 to 10 min after the infusion, and 10 to 20 min after the infusion. The experiment was terminated at the end of each period. The Ki value was calculated.

Autoradiography was conducted as follows: The frozen brains were mounted onto pedestals with M-1 embedding matrix, and 20 μm coronal sections were cut with a cryotome. The sections were thawmounted onto cover slips, and autoradiograms were generated by coexposing the sections on Kodak XAR-5 film with tissue-calibrated $^{14}$C standards for 2 weeks. The sequential section was stained with hematoxylin for correlation of areas of histologically verified tumor with autoradiograms. The regional radioactivities were measured in tumor, brain surrounding the tumor (BST; areas at around 2 mm distance from the border of the tumor), ipsilateral cortex to tumor, contralateral cortex, ipsilateral white matter (WM), contralateral WM, ipsilateral basal ganglia (BGG), and contralateral BGG. Quantitative analysis of the regional radioactivity was performed using a computer (Macintosh II) with a scanner (UMAX) UC$_{630}$ and the software, Image 1.45 (NIH).

Figure 3:
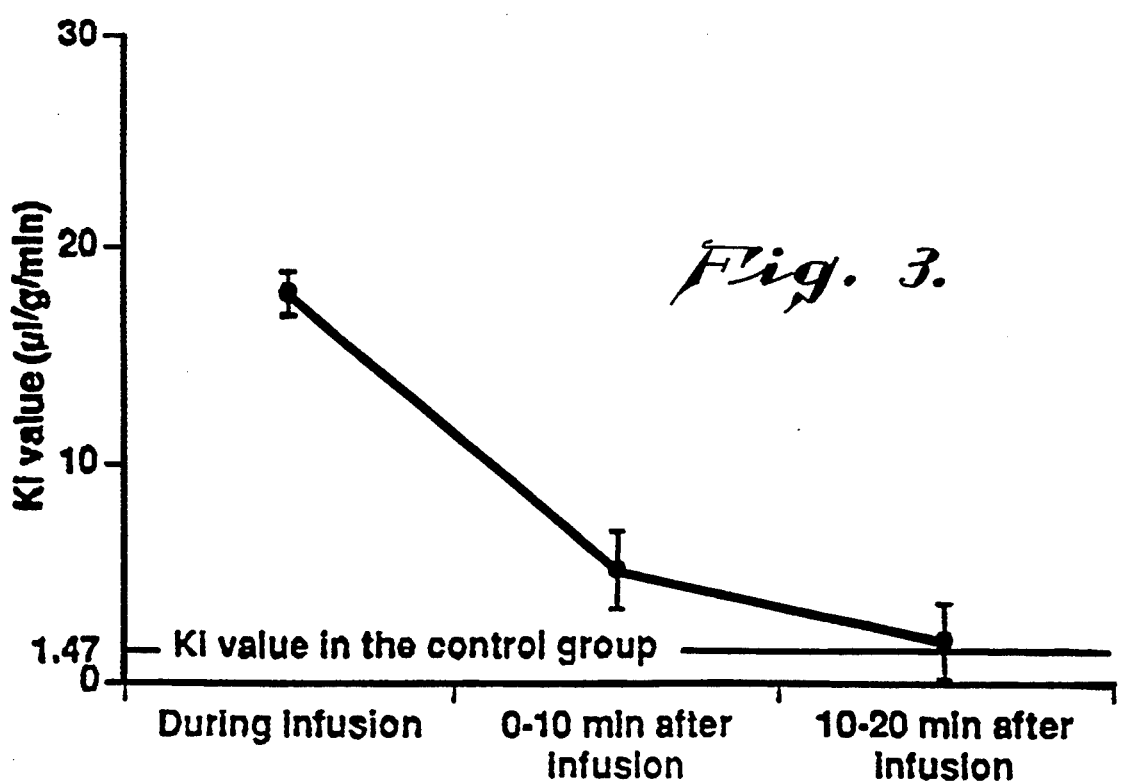
FIG. 3 depicts test results showing the decrease in blood-tumor barrier permeability during the time period following infusion of bradykinin into the carotid artery in accordance with the present invention. The effect is reversible approximately 20 minutes after stopping the infusion of bradykinin.

The effect of bradykinin on tumor permeability was diminished 20 minutes after stopping the intracarotid bradykinin infusion (FIG. 3). The degradation of bradykinin in rats has been reported to be on the order of several hours (18). The shorter effect of bradykinin on tumor capillary permeability is believed to be due to both the selective intracarotid infusion and the lower does of bradykinin used. The short effect on tumor capillaries of intracarotid infusion of bradykinin is, desirable for the selective delivery of anticancer drug in the treatment of the brain tumors.

The enzyme that degrades bradykinin is peptidyl carboxypeptidase kinase II, which is identical to angiotensin I converging enzyme (ACE) (19). Williams, et al., using antiserum to the purified pig kidney ACE, reported that the pig brain capillary contained ACE (20). Moreover, the ACE inhibitor, captopril, enhanced the bradykinin effect (14, 21). Whether the rat brain capillary had ACE was examined using antiserum to the purified human kidney ACE. Angiotensin converting enzyme was not recognized in the rat brain capillaries, whereas this antiserum recognized ACE in the rat kidney cortex. When an intravenous captopril infusion was used to enhance the effects of bradykinin on tumor permeability, hypotension occurred which made it difficult to maintain normal systemic pressure.

Microscopic analysis was performed using intravenously injected horseradish peroxidase (HRP) as described in (22). After rat preparation as previously described, bradykinin (10 μg/Kg/min in saline) or saline as a control was injected into the right carotid artery for 15 minutes. Five minutes after the start of the intracarotid infusion, 20 mg/100g of horseradish peroxidase (HRP) was injected by an intravenous bolus. Ten minutes after the HRP injection rats were perfused with a mixture of 2% glutaraldehyde and 2% formaldehyde in 0.1 sodium phosphate buffer solution at pH 7.4 through the heart. After fixation, the brains were removed and cut at 40 μm thickness on a vibratome. The sections were preincubated for 15 min at room temperature in the medium consisting of 10 ml 0.05 M-Tris-HCl buffer (pH 7.4), 3,3'-diaminobenzidine tetrahydrochloride and 0.02% hydrogen peroxide (Sigma). The sections were trimmed down to the areas of interests, postfixed for 2 hr in 2% osmium tetroxide with 0.1 M sodium phosphate, dehydrated, and embedded in plastic. Plastic sections 1 μm thick were observed under light microscopy.

The HRP stain was well recognized in the extracellular space between tumor cells in the bradykinin group, whereas the HRP stain was much less in the control group. In normal brain, bradykinin increased the HRP staining within the cytoplasm of only a few endothelial cells and there was no extravasation of HRP between cells. The effect of low dose bradykinin on endocytosis in endothelial cells in normal brain is, therefore, small. It has been reported that the nanomolar concentrations of bradykinin stimulated the uptake of the fluorescent marker, Lucifer yellow, in the brain capillary endothelial cells by 40% (23). It also has been reported that high dose intracarotid infusion of bradykinin (almost 6 times higher than the dose of the present invention, caused extravasation of HRP around the normal brain capillary. Vasodilatation of microvessels and HRP endocytosis in endothelial cells was also recognized. The tight junctions of the endothelium were intact (16). In the above example, the HRP stain was limited to a few endothelial cells in the bradykinin group. This demonstrates that in contrast to other studies using high dose bradykinin, lower doses of bradykinin in accordance with the present invention selectively increase the tumor permeability without increasing the normal brain permeability.

To demonstrate that bradykinin could selectively deliver other high molecular weight compounds into tumors. Evans blue (EB) was injected intravenously instead of radiolabeled tracers as follows: After the preparation of rats as previously described, 2 ml/kg of 2% Evans Blue (EB) was injected intravenously as also described above. After the intracarotid bradykinin infusion, the rat was perfused with 200 ml of phosphate buffer through the heart to wash out the remaining EB from the vessels. The brains were removed immediately and cut as coronal sections.

Since EB binds to serum albumin (MW 67,000) in blood and distributes with albumin in vivo, EB staining in the tissue indicates the distribution of albumin (4). In order to observe the extravasated EB and not the EB remaining in the vessels in the brain, the blood from the brain was washed out by perfusing the rats with phosphate buffer from the heart. The EB staining was well recognized in the tumor but not in the normal brain of the bradykinin group. Much less staining was seen in the control group. This shows that intracarotid bradykinin infusion selectively increased the delivery of EB albumin to the tumor.

The above examples demonstrate the use of intracarotid bradykinin infusion as a method to selectively deliver high molecular weight agents to brain tumors. Intracarotid bradykinin infusion at low doses increases the permeability for the high molecular weight tracer dextran by 12-fold, and for low molecular weight tracer AIB by 1.8 fold. Moreover, selective extravasation of HRP and EB staining in tumors were caused by intracarotid bradykinin infusion. Accordingly, the method of the present invention is useful for selectively delivering large molecular weight compounds to brain tumors.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

BIBLIOGRAPHY

1. Kumagai A. K., Eisenberg J. B., Pardridge W. M.: Absorptive-mediated endocystosis of cationized albumin and a β-endorphin-cationized albumin chimeric peptide by isolated brain capillaries. Model system of blood-brain barrier transport. *J Biol Chem* 262: 15214–15219, 1987.
2. Neuwelt E. A., Barnett P. A., McCormick C. I., et al.: Osmotic blood-brain barrier modification: monoclonal antibody, albumin, and methotrexate delivery to cerebrospinal fluid and brain. *Neurosurgery* 17:419–423, 1985.
3. Neuwelt E. A., Hill S. A., Frenkel E. P.: Osmotic blood-brain barrier modification and combination chemotherapy: concurrent tumor regression in areas of barrier opening and progression in regions distant to barrier opening. *Neurosurgery* 15: 362–366, 1984.
4. Pardridge W. M., Kumagai A. K., Eisenberg J. B.: Chimeric peptides as a vehicle for peptide pharmaceutical delivery through the blood-brain barrier. *Biochem Biophys Res Commun* 146:307–313, 1987.
5. Iomiwa K, Hazama F., Mikawa H: Neurotoxicity of vincristine after osmotic opening of the blood-brain barrier. *Neuropathol Appl Neurobiol* 9:345–354, 1983.
6. Black K. L., Betz A. L., Ar D. B.: Leukotriene $C_4$ receptors in isolated brain capillaries. *Adv Protaglandin Thromboxine Leukotriene Res* 17:508–511, 1987.
7. Black K. I., Hoff J. T.: Leukotrienes and blood-brain barrier permeability: *Cereb Flow Metab* 5 (Suppl): 263–264, 1985.
8. Black K. L., Hoff J. T.: Leukotrienes increase blood-brain barrier permeability following intraparenchymal injections in rats. *Ann Neurol* 18:349–351, 1985.
9. Black K. L., Hoff J. T., McGillicuddy J. E., et al: Increased leukotriene $C_4$ and vasogenic edema surrounding brain tumors in humans. *Ann Neurol* 19:592–595, 1986.
10. Black K. L., Chio C. C.: Increased Opening of Blood-Tumour Barrier by Leukotriene $C_4$ is Dependent on Size of Molecules. *Neurological Research Vol* 74, December 1982, pp. 402–404.
11. Black, K. L., King W. A., Ikezaki K: Selective Opening of the Blood Tumor Barrier by Intracarotid Infusion of Leukotriene $C_4$. *J. Neurosurg, Vol.* 72, June 1990, pp. 912–916.
12. Baba T, Black K. L., Ikezaki K, Chen K, Becker D. P.: Intracarotid Infusion of Leukotriene $C_4$ Selectively Increases Blood-Brain Permeability After Focal Ischemia in Rats. *J Cereb Blood Flow Metab.* Vol. 11, No. 4, 1991.
13. Chio C. C., Baba T, Black K. L.: Selective Blood-Tumor Barrier Description By Leukotrienes. *J. Neurosurg. Vol.* 77, September 1992.
14. Yong T, et al., *Circ Res* 70, 952 (1992).
15. Alvarez A. L., et al., *Clin Sci* 82, 513 (1992).
16. Raymond J. J., Robertson D. M., Dinsdale H. B., *Can J Neurol Sci* 13, 214 (1986).
17. Erdos E. G., *J Cardiovasc Pharmacol* 15, 820 (1990).; Vanhoutee P. M., et al., *Br J Clin Pharmacol* 28, 95 (1989).
18. Kumakura S, Kamo I, Tsurufuju S, *Br J Pharmacol* 93, 739 (1988).
19. Ng K. K. F., Vane J. R., *Nature* 216, 762 (1967).
20. Williams T. A., Hooper N. M., T. A. J., *J Neurochem* 57, 193 (1991).
21. Mombouli J. V., Illiano S, Nagao T, Scott B. T., Vanhoutte P. M., *Circ Res* 71, 137 (1992).
22. Nishio S, Ohta M, Abe M, Kitamura K, *Acta Neuropathol (Berl)* 59, 1 (1983).
23. Guillot F. L., Audus K. L., *J Cereb Blood Flow Metab* 827 ( 1990 ).
24. Dobbin J, Crockard H. A., Ross R. R., *J Cereb Blood Flow Metab* 9, 71 (1989).

What is claimed is:

1. A method for selectively delivering a neuropharmaceutical or diagnostic agent to abnormal brain tissue present in a mammal, said method comprising the steps of:
    providing a mammal which has normal brain tissue and abnormal brain tissue, said abnormal brain tissue resulting from a tumor, multiple sclerosis, ischemia, cerebral abscess, inflammation, infection or degeneration and wherein said normal brain tissue comprises normal brain tissue capillaries and said abnormal brain tissue comprises abnormal brain tissue capillaries;
    infusing bradykinin or a bradykinin analog into the carotid artery of said mammal, said bradykinin or bradykinin analog being infused in an amount of between about 0.05 μg/Kg/minute body weight and 20 μg/Kg body weight/minute; and administering to said mammal a therapeutic amount of a neuropharmaceutical agent which is selected from the group consisting of cisplatin, carboplatin, methotrexate, 5-FU, amphotericin and monoclonal antibodies wherein said neuropharmaceutical agent is selectively delivered to said abnormal tissue present in said mammal.

2. A method according to claim 1 wherein said bradykinin or bradykinin analog is infused into said carotid artery over a period of between about 5 minutes to about 20 minutes.

3. A method according to claim 1 wherein said neuropharmaceutical agent is administered simultaneously with the infusion of bradykinin or bradykinin analog.

4. A method for selectively delivering a neurodiagnostic agent to abnormal brain tissue present in a mammal, said method comprising the steps of:
   providing a mammal which has normal brain tissue and abnormal brain tissue, said abnormal brain tissue resulting from a tumor, multiple sclerosis, ischemia, cerebral abscess, inflammation, infection or degeneration and wherein said normal brain tissue comprises normal brain tissue capillaries and said abnormal brain tissue comprises abnormal brain tissue capillaries;
   infusing bradykinin or a bradykinin analog into the carotid artery of said mammal, said bradykinin or bradykinin analog being infused in an amount of between about 0.05 $\mu$g/Kg/minute body weight and 20 $\mu$g/Kg body weight/minute; and
   administering to said mammal a diagnostic amount of a neurodiagnostic agent which is selected from the group consisting of 99-Tc glucoheptonate, gallium-EDTA, ferrous magnetic contrast agents and iodinated contrast agents wherein said neurodiagnostic agent is selectively delivered to said abnormal tissue present in said mammal.

5. A method according to claim 4 wherein said bradykinin or bradykinin analog is infused into said carotid artery over a period of between about 5 minutes to about 20 minutes.

6. A method according to claim 4 wherein said neurodiagnostic agent is administered simultaneously with the infusion of bradykinin or bradykinin analog.

* * * * *

UNITED STATES PATENT AND TRADEMARK OFFICE
CERTIFICATE OF CORRECTION

PATENT NO. : 5,434,137
DATED : July 18, 1995
INVENTOR(S) : Black, Keith L.

It is certified that error appears in the above-indentified patent and that said Letters Patent is hereby corrected as shown below:

Column 5, line 63, "$UC_{630}$" should be "UC630"

Column 8, line 67, "0.5 µg/Kg/minute body weight" should be "0.5 µg/Kg/body weight/minute"

Column 10, line 6, "0.5 µg/Kg/minute body weight" should be "0.5 µg/Kg/body weight/minute"

Signed and Sealed this

Twenty-fourth Day of October, 1995

Attest:

BRUCE LEHMAN

Attesting Officer  Commissioner of Patents and Trademarks